(12) United States Patent
Sumida et al.

(10) Patent No.: US 9,404,144 B2
(45) Date of Patent: *Aug. 2, 2016

(54) GLUCOSE DEHYDROGENASE

(71) Applicant: TOYOBO CO., LTD., Osaka-shi, Osaka (JP)

(72) Inventors: Yosuke Sumida, Tsuruga (JP); Rie Hirao, Tsuruga (JP); Yuu Utashima, Tsuruga (JP); Hiroshi Kawaminami, Tsuruga (JP); Hiroshi Aiba, Tsuruga (JP); Takahide Kishimoto, Tsuruga (JP); Shusaku Yanagidani, Tsuruga (JP)

(73) Assignee: TOYOBO CO., LTD., Osaka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/374,164

(22) PCT Filed: Feb. 7, 2013

(86) PCT No.: PCT/JP2013/052798
§ 371 (c)(1),
(2) Date: Jul. 23, 2014

(87) PCT Pub. No.: WO2013/118798
PCT Pub. Date: Aug. 15, 2013

(65) Prior Publication Data
US 2015/0031059 A1    Jan. 29, 2015

(30) Foreign Application Priority Data

Feb. 9, 2012  (JP) ................................. 2012-026392
Feb. 9, 2012  (JP) ................................. 2012-026415

(51) Int. Cl.
| | | |
|---|---|---|
| C12N 9/04 | (2006.01) | |
| C12N 15/53 | (2006.01) | |
| C12Q 1/32 | (2006.01) | |
| C12Q 1/54 | (2006.01) | |

(52) U.S. Cl.
CPC ................. *C12Q 1/54* (2013.01); *C12N 9/0006* (2013.01); *C12Q 1/32* (2013.01); *C12Y 101/05* (2013.01); *C12Y 101/01047* (2013.01); *G01N 2333/904* (2013.01)

(58) Field of Classification Search
CPC ........... C12Q 1/32; C12Q 1/006; C12Q 1/54; C12Y 101/9901
USPC ............................. 435/14, 254.8; 204/403.14
See application file for complete search history.

(56) References Cited

U.S. PATENT DOCUMENTS

| | | | |
|---|---|---|---|
| 7,067,295 B1 * | 6/2006 | Sode .............. | 435/190 |
| 8,445,246 B2 * | 5/2013 | Tajima et al. ............ | 435/183 |
| 2006/0063217 A1 | 3/2006 | Omura et al. | |
| 2008/0220460 A1 | 9/2008 | Kawaminami et al. | |
| 2009/0176262 A1 | 7/2009 | Omura et al. | |
| 2009/0317848 A1 | 12/2009 | Kawaminami et al. | |
| 2010/0297743 A1 | 11/2010 | Omura et al. | |
| 2011/0318810 A1 * | 12/2011 | Tajima et al. .............. | 435/190 |
| 2012/0122130 A1 | 5/2012 | Omura et al. | |
| 2012/0171708 A1 | 7/2012 | Kawaminami et al. | |
| 2012/0244565 A1 | 9/2012 | Nishio et al. | |
| 2013/0168263 A1 | 7/2013 | Sode et al. | |
| 2014/0057331 A1 | 2/2014 | Tajima et al. | |

FOREIGN PATENT DOCUMENTS

| | | |
|---|---|---|
| JP | 2007-289148 A | 11/2007 |
| JP | 2008-237210 A | 10/2008 |
| WO | 2004/058958 A1 | 7/2004 |
| WO | 2006/101239 A1 | 9/2006 |
| WO | 2008/059777 A1 | 5/2008 |
| WO | 2010/053161 A1 | 5/2010 |
| WO | 2010-140431 A1 | 12/2010 |
| WO | 2011/034108 A1 | 3/2011 |
| WO | 2011/068050 A1 | 6/2011 |
| WO | 2012/001976 A1 | 1/2012 |
| WO | 2012/073986 A1 | 6/2012 |

OTHER PUBLICATIONS

International Search Report dated Mar. 5, 2013 issued in corresponding application No. PCT/JP2013/052798.
Bak et al., "Studies on the Glucose Dehydrogenase of Aspergillus Oryzae", Biochim.Biophys.Acta, vol. 139, No. 2, 1967, pp. 265-276.
Bak, "Studies on Glucose Dehydrogenase of Aspergillus Oryzae", Biochim.Biophys.Acta, vol. 139, No. 2, 1967, pp. 277-293.
Bak., "Studies on Glucose Dehydrogenase of Aspergillus Oryzae", Biochinn.Biophys.Acta, vol. 146, No. 2, 1967, pp. 317-327.
Bak et al., "Studies on Glucose Dehydrogenase of Aspergillus Oryzae", Biochim.Biophys.Acta, vol. 146, No. 2, 1967, pp. 328-335.
Hayano et al., "Purification and Properties of 3-Ketosucrose-forming Enzyme from the Cells of Agrobacterium tumefaciens", The Journal of Biological Chemistry, vol. 242, No. 16, Aug. 25, 1967, pp. 3665-3672.
Tsugawa et al., "Purification of a Marine Bacterial Glucose Dehydrogenase from Cytophaga marinoflava and its Application for Measurement of 1,5-Anhydro-D-Glucitol", Applied Biochemistry and Biotechnology, vol. 56, 1996, pp. 301-310.

* cited by examiner

*Primary Examiner* — Robert Mondesi
*Assistant Examiner* — Younus Meah
(74) *Attorney, Agent, or Firm* — Westerman, Hattori, Daniels & Adrian, LLP

(57) ABSTRACT

An object of the present invention is to provide a novel glucose dehydrogenase, a method for producing the glucose dehydrogenase, and applications of the glucose dehydrogenase. The flavin-binding glucose dehydrogenase of the invention has the following characteristics (1) and (4): (1) Molecular weight: the molecular weight of a polypeptide moiety in the enzyme is about 68 kDa as measured by SDS-polyacrylamide electrophoresis; (2) Km value: the Km value for D-glucose is about 15 mM or less; (3) Temperature stability: stable at a temperature of 55° C. or less; and (4) pH stability: stable at a pH range of 3.0 to 8.5.

14 Claims, 3 Drawing Sheets

GLUCOSE DEHYDROGENASE

TECHNICAL FIELD

The present invention relates to a glucose dehydrogenase. Specifically, the invention relates to a flavin-binding glucose dehydrogenase, DNA encoding the flavin-binding glucose dehydrogenase, a fungus that produces the flavin-binding glucose dehydrogenase, a method for producing the flavin-binding glucose dehydrogenase, a method for measuring glucose using the flavin-binding glucose dehydrogenase, and the like.

BACKGROUND ART

Self-monitoring of blood glucose (SMBG) is important for diabetic patients to manage their blood glucose levels and to use this monitoring in treatment. Simple blood glucose self-monitoring devices using an electrochemical biosensor have recently been widely used in SMBG. The biosensor includes an insulating substrate on which electrodes and an enzyme reaction layer are formed.

Examples of enzymes used herein include glucose dehydrogenase (GDH), glucose oxidase (GO), and the like. In terms of methods using GO (EC 1.1.3.4), a problem has been noted in that dissolved oxygen in a measurement sample is likely to affect the measurement results. Although GDH is unaffected by dissolved oxygen, it is not suitable for accurately measuring blood glucose levels, because, for example, a pyrroloquinoline quinone-dependent glucose dehydrogenase (PQQ-GDH) (EC1.1.5.2 (formerly EC1.1.99.17)) acts on sugars, such as maltose and lactose, in addition to glucose.

A flavin adenine dinucleotide-dependent glucose dehydrogenase (hereinafter also referred to as "FADGDH") is unaffected by dissolved oxygen and has almost no action on maltose. Patent Documents 1 to 6 and Non-patent Documents 1 to 6 report enzymes derived from *Aspergillus terreus* and *Aspergillus oryzae*, and modifications of these. These enzymes, however, have relatively high reactivity to xylose (Patent Document 1), and there is therefore room for improvement in measuring blood glucose of people who are undergoing a xylose tolerance test. Further, a flavin-binding GDH having relatively low action on xylose (Patent Document 6), a modified GDH having combined advantages of GO and GDH (Patent Document 7), and the like, have recently been developed; however, there is still room for improvement.

CITATION LIST

Patent Documents

Patent Document 1: WO2004/058958
Patent Document 2: WO2006/101239
Patent Document 3: JP2007-289148A
Patent Document 4: JP2008-237210A
Patent Document 5: WO2008/059777
Patent Document 6: WO2010/140431
Patent Document 7: WO2011/068050

Non-Patent Documents

Non-patent Document 1: Biochim Biophys Acta. 1967 Jul. 11; 139 (2): 265-76
Non-patent Document 2: Biochim Biophys Acta. 1967 Jul. 11; 139 (2): 277-93
Non-patent Document 3: Biochim Biophys Acta. 146 (2): 317-27
Non-patent Document 4: Biochim Biophys Acta. 146 (2): 328-35
Non-patent Document 5: J Biol Chem (1967) 242: 3665-3672
Non-patent Document 6: Appl Biochem Biotechnol (1996) 56: 301-310

SUMMARY OF INVENTION

Technical Problem

Under the above circumstances, the present inventors conducted intensive research to develop a novel glucose dehydrogenase that is more suitable for use in SMBG, and found that the use of an enzyme that has excellent substrate specificity, high affinity for D-glucose, and excellent stability enables shortening the measurement time while accurately measuring blood glucose levels with a small amount of enzyme. Further, the production of SMBG sensors that use enzymes generally involves a heat treatment process. Therefore, in addition to the above characteristics, the enzymes desirably have excellent thermal stability so that the enzyme activity is not abolished by heat treatment. In view of this, an object of the invention is to provide a novel glucose dehydrogenase having excellent substrate specificity, high affinity for a substrate, and excellent thermal stability, thus being suitable for use in SMBG sensors.

Solution to Problem

The present inventors conducted intensive research to achieve the above object. As a result of screening many microorganisms that had not been reported to produce glucose dehydrogenase, they found that novel microorganisms have glucose dehydrogenase activity. The present inventors then isolated and purified this enzyme, analyzed its characteristics, and thereby found that the enzyme was a flavin-binding glucose dehydrogenase that has excellent substrate specificity, high affinity for D-glucose, and excellent thermal stability. Further, the present inventors determined the amino acid sequence and gene sequence of the isolated enzyme, and ascertained that these sequences are different from those of already reported FADGDH, and that the isolated enzyme is novel.

The present inventions have been accomplished as a result of further research and improvement based on these findings. Representative examples of the invention are described below.

Item 1. A flavin-binding glucose dehydrogenase comprising any one of the following polypeptides (a) to (c):
(a) a polypeptide having an amino acid sequence of SEQ ID NO: 1;
(b) a polypeptide having the amino acid sequence of SEQ ID NO: 1 in which one or several amino acid residues are substituted, deleted, inserted, added, and/or inverted, and having glucose dehydrogenase activity; and
(c) a polypeptide having an amino acid sequence with 80% or more identity to the amino acid sequence of SEQ ID NO: 1, and having glucose dehydrogenase activity.

Item 2. A DNA of any one of the following (A) to (F):
(A) DNA encoding an amino acid sequence of SEQ ID NO: 1;
(B) DNA having a base sequence of SEQ ID NO: 2;
(C) DNA having a base sequence with 80% or more homology to the base sequence of SEQ ID NO: 2, and encoding a polypeptide having glucose dehydrogenase activity;

(D) DNA hybridizing to a base sequence complementary to the base sequence of SEQ ID NO: 2 under stringent conditions, and encoding a polypeptide having glucose dehydrogenase activity;

(E) DNA having the base sequence of SEQ ID NO: 2 in which one or several bases are substituted, deleted, inserted, added, and/or inverted, and encoding a polypeptide having glucose dehydrogenase activity; and (F) DNA having the amino acid sequence of SEQ ID NO: 1 in which one or several amino acid residues are substituted, deleted, inserted, added, or inverted, and encoding a polypeptide having glucose dehydrogenase activity.

Item 3. A vector containing the DNA of Item 2.

Item 4. A transformant containing the vector of Item 3.

Item 5. A method for producing the flavin-binding glucose dehydrogenase of Item 1, the method comprising culturing the transformant of Item 4.

Item 6. A method for measuring a glucose concentration, the method comprising causing the flavin-binding glucose dehydrogenase of Item 1 to act on glucose.

Item 8. A glucose assay kit comprising the flavin-binding glucose dehydrogenase of Item 1.

Item 9. A glucose sensor comprising the flavin-binding glucose dehydrogenase of Item 1.

Item A. A flavin-binding glucose dehydrogenase having the following characteristics (1) to (4):

(1) Molecular weight: the molecular weight of a polypeptide moiety in the enzyme is about 68 kDa as measured by SDS-polyacrylamide electrophoresis;

(2) Km value: the Km value for D-glucose is about 15 mM or less;

(3) Temperature stability: stable at a temperature of 55° C. or less; and (4) pH stability: stable at a pH range of 3.0 to 8.5.

Item B. The flavin-binding glucose dehydrogenase according to Item A, further having the following characteristic (5):

(5) Substrate specificity: the reactivity to D-xylose is 1.5% or less, based on the reactivity to D-glucose taken as 100%.

Item C. The flavin-binding glucose dehydrogenase according Item A or B, further having the following characteristic (6):

(6) Optimal activity temperature: 50 to 55° C.

Item D. The flavin-binding glucose dehydrogenase according to any one of Items A to C, further having the following characteristic (7):

(7) Optimal activity pH: 8.0.

Item E. The flavin-binding glucose dehydrogenase according to any one of Items A to D, further having the following characteristic (8):

(8) Origin: the enzyme is derived from microorganisms of the genus *Mucor*.

Item F. A method for producing the flavin-binding glucose dehydrogenase of any one of Items A to E, the method comprising:

culturing microorganisms of the genus *Mucor*; and recovering a glucose dehydrogenase.

Item G. A method for measuring a glucose concentration, the method comprising causing the flavin-binding glucose dehydrogenase of any one of Items A to E to act on glucose.

Item H. A glucose assay kit comprising the flavin-binding glucose dehydrogenase of any one of Items A to E.

Item I. A glucose sensor comprising the flavin-binding glucose dehydrogenase of any one of Items A to E.

Advantageous Effects of Invention

The flavin-binding glucose dehydrogenase (hereinafter sometimes referred to as "FGDH") of the invention has glucose dehydrogenase activity and high affinity for D-glucose (i.e., has a significantly small Km value for D-glucose), and thus enables measurement of D-glucose concentration in a sample in a shorter period of time with a smaller amount of enzyme. Additionally, since the FGDH of the invention has significantly reduced reactivity to D-xylose, even when D-glucose and D-xylose are both present in a sample, the amount and the concentration of glucose can be accurately measured. The FGDH of the invention is therefore suitable for measuring blood glucose levels of people who are undergoing a xylose tolerance test. Further, the FGDH of the invention has excellent thermal stability and thus enables production of efficient sensor strips that involves heat treatment. Also, the FGDH of the invention is stable within a wide pH range, and thus it can be suitably used under a wide range of conditions. With these characteristics, the FGDH of the invention makes it possible to accurately measure glucose concentration in any sample containing D-glucose (e.g., blood and food (such as seasonings and beverages)). Further, the DNA of the invention encodes the FGDH of the invention, and the FGDH of the invention can thus be efficiently produced by using genetic engineering techniques.

DESCRIPTION OF EMBODIMENTS

Figure 1:
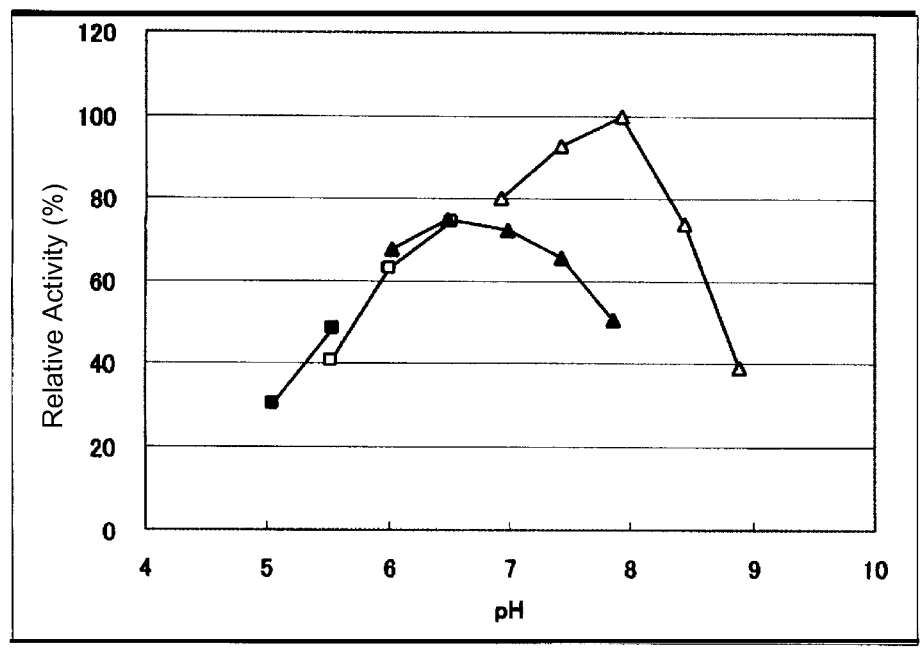
FIG. 1 is a graph showing the influence of pH on the activity of RD056860-derived FGDH.

The present invention is described below in detail.

1. Flavin-Binding Glucose Dehydrogenase 1-1. Glucose Dehydrogenase Activity

A flavin-binding glucose dehydrogenase is an enzyme that has a physicochemical property such that it catalyzes a reaction in which hydroxy groups of glucose are oxidized to produce glucono-δ-lactone in the presence of an electron acceptor. In this specification, this physicochemical property represents glucose dehydrogenase activity, and the terms "enzyme activity" and "activity" represent this enzyme activity, unless otherwise noted. The electron acceptor is not limited as long as it can accept electrons in a reaction catalyzed by FGDH. For example, 2,6-dichlorophenolindophenol (DCPIP), phenazine methosulfate (PMS), 1-methoxy-5-methylphenazium methylsulfate, and ferricyanide compounds may be used.

The glucose dehydrogenase activity can be measured by known methods. For example, the activity can be measured using DCPIP as an electron acceptor and based on the change in absorbance of a sample at a wavelength of 600 nm before and after the reaction. More specifically, the activity can be measured using the following reagent and under the following measurement conditions.

Method for Measuring Glucose Dehydrogenase Activity

Reagent 50 mM PIPES buffer solution, pH of 6.5 (containing 0.1% TritonX-100)

24 mM PMS solution 2.0 mM 2,6-dichlorophenolindophenol (DCPIP) solution

1 M D-glucose solution

The reaction reagent is obtained by mixing 20.5 mL of the PIPES buffer solution, 1.0 mL of the DCPIP solution, 2.0 mL of the PMS solution, and 5.9 mL of the D-glucose solution.

Measurement Conditions

The reaction reagent (3 mL) is preheated at 37° C. for 5 minutes. An FGDH solution (0.1 mL) is added and gently mixed. Water is used as a control, and changes in absorbance at 600 nm are recorded for 5 minutes by a spectrophotometer at a controlled temperature of 37° C. Based on the linear portion (i.e., after the reaction rate becomes constant), the change in absorbance per minute ($\Delta OD_{TEST}$) is measured. In a blind test, a solvent used for dissolving FGDH is added to the reagent mixture in place of the FGDH solution, and the change in absorbance per minute ($\Delta OD_{BLANK}$) is measured in a similar manner. Based on the obtained values, the FGDH activity is determined by the following equation. Here, one unit (U) of the FGDH activity is equal to the enzyme amount that reduces 1 μmol of DCPIP in 1 minute in the presence of D-glucose at a concentration of 200 mM.

$$\text{Activity (U/mL)} = \{-(\Delta OD_{TEST} - \Delta OD_{BLANK}) \times 3.1 \times \text{dilution rate}\} / \{16.3 \times 0.1 \times 1.0\}$$

In the equation, 3.1 is the total liquid amount (mL) of the reaction reagent and the enzyme solution, 16.3 is the millimolar extinction coefficient ($cm^2/\mu mol$) under conditions in which the activity is measured, 0.1 is the amount (mL) of the enzyme solution, and 1.0 is the optical path length (cm) of the cell. In this specification, the enzyme activity is measured according to the above measurement method, unless otherwise indicated.

The FGDH of the invention refers to flavin-binding GDH, which requires flavin as a prosthetic group. In this specification, the flavin-binding GDH is also referred to as "FGDH."

The FGDH of the invention is preferably isolated FGDH or purified FGDH. The FGDH of the invention may be in a state of being dissolved in a solution described above that is suitable for storage or in a freeze-dried state (e.g., powder). The expression "isolated" used in regard to the enzyme (FGDH) of the invention refers to a state in which the enzyme is substantially free of components (e.g., host-cell-derived contaminating proteins, other components, and culture media) other than the enzyme. Specifically, for example, the isolated enzyme of the invention contains contaminating proteins in an amount of less than about 20%, preferably less than about 10%, more preferably less than about 5%, even more preferably less than about 1%, of the total (by weight). It is also possible for the FGDH of the invention to be present in a solution (e.g., buffer) suitable for storage or for measurement of enzyme activity.

1-2. Polypeptide

The FGDH of the invention preferably comprises any one of the following polypeptides (a) to (c):

(a) a polypeptide having the amino acid sequence of SEQ ID NO: 1;

(b) a polypeptide having the amino acid sequence of SEQ ID NO: 1 in which one or several amino acid residues are substituted, deleted, inserted, added, and/or inverted, and having glucose dehydrogenase activity; and (c) a polypeptide having an amino acid sequence with 80% or more identity to the amino acid sequence of SEQ ID NO: 1, and having glucose dehydrogenase activity.

As shown in Example 5, the amino acid sequence of SEQ ID NO: 1 is equal to the amino acid sequence of FGDH derived from *Mucor* RD056860. The RGDH derived from *Mucor* RD056860 exhibits all the characteristics described in Sections 1-3 to 1-10 below.

The polypeptide described in (b) above has the amino acid sequence of SEQ ID NO: 1 in which one or several amino acid residues are substituted, deleted, inserted, added, and/or inverted (hereinafter sometimes collectively referred to as "mutation"), as long as the glucose dehydrogenase activity is not impaired. The term "several" as used herein indicates a number corresponding to, for example, less than about 20%, preferably less than about 15%, still more preferably less than about 10%, even more preferably less than about 5%, and the most preferably less than about 1%, of the total amino acids, although such a number is not limited as long as the glucose dehydrogenase activity and preferably the characteristics described in Sections 1-3 to 1-10 (in particular, Sections 1-3, 1-4, 1-7, and 1-8) below are not impaired. More specifically, the number of mutated amino acid residues is, for example, 2 to 127, preferably 2 to 96, more preferably 2 to 64, still more preferably 2 to 32, even more preferably 2 to 20, further preferably 2 to 15, yet further preferably 2 to 10, and the most preferably 2 to 5.

When the mutation is amino acid substitution, the type of amino acid substitution is not particularly limited, but is preferably a conservative amino acid substitution, because it does not cause a significant effect on the phenotype of FGDH. "Conservative amino acid substitution" refers to a replacement of an amino acid residue with another amino acid residue having a side chain with similar properties. Amino acid residues are grouped into various families according to their side chains, such as basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). Therefore, a replacement between amino acid residues of the same family is preferable.

One or more mutations can be performed by introducing one or more mutations into DNA encoding the FGDH of the invention (mentioned below) by using known techniques, such as restriction enzyme treatment, treatment with exonuclease, DNA ligase, or the like, a site-directed mutagenesis induction method (Molecular Cloning, Third Edition, Chapter 13, Cold Spring Harbor Laboratory Press, New York), a random mutagenesis introduction method (Molecular Cloning, Third Edition, Chapter 13, Cold Spring Harbor Laboratory Press, New York), and the like. Other methods, such as ultraviolet irradiation, may also be used to produce variant FGDH. Variant FGDH also includes, for example, naturally occurring variants (e.g., single nucleotide polymorphism), based on individual variability of microorganisms carrying FGDH, or on difference in species or families of those microorganisms.

In terms of maintaining the FGDH activity, the one or more mutations above preferably present in sites that do not influence the FGDH active site or substrate binding site.

The polypeptide described in (c) above is a polypeptide having an amino acid sequence with 80% or more identity to the amino acid sequence of SEQ ID NO: 1, as long as the glucose dehydrogenase activity and preferably the characteristics described in Sections 1-3 to 1-10 above (in particular, Sections 1-3, 1-4, 1-7, and 1-8) are maintained. The amino acid sequence of the FGDH of the invention preferably has 85% or more, more preferably 88% or more, still more preferably 90% or more, even more preferably 93% or more, further preferably 95% or more, particularly preferably 98% or more, and the most preferably 99% or more, identity to the amino acid sequence of SEQ ID NO: 1. A polypeptide having an amino acid sequence with the certain degree of identity can be produced based on known genetic engineering techniques mentioned above.

The amino acid sequence identity can be calculated using a commercially available analytical tool or an analytical tool available through telecommunication lines (Internet). For example, the online homology algorithm Basic Local Alignment Search Tool (BLAST program) of the National Center for Biotechnology Information (NCBI), available at www.ncbi.nlm.nih.gov/BLAST/, may be used for the calculation using parameters with default (initial) settings.

1-3. Substrate Specificity

The FGDH of the invention has excellent substrate specificity. In particular, the FGDH of the invention has significantly reduced reactivity at least to D-xylose, compared to the reactivity to D-glucose. More specifically, the FGDH of the invention has reactivity to D-xylose of preferably 1.5% or less, based on the reactivity to D-glucose at the same concentration taken as 100%.

In addition to the low reactivity to D-xylose, it is preferable that the FGDH of the invention also has low reactivity to D-galactose and maltose. The FGDH of the invention has reactivity to D-galactose of generally 5% or less, preferably 3% or less, more preferably 2% or less, still more preferably 1.5% or less, and particularly preferably 1.2% or less, based on the reactivity to D-glucose at the same concentration taken as 100%.

The FGDH of the invention has reactivity to maltose of generally 5% or less, preferably 4% or less, more preferably 3% or less, and still more preferably 2.5% or less, based on the reactivity to D-glucose at the same concentration taken as 100%.

The lower limit of the reactivity of the FGDH of the invention to D-xylose, D-galactose, or maltose, based on the reactivity to D-glucose, is not particularly limited, but may be set to 0% or a value closest to 0%.

The reactivity of FGDH to each sugar can be measured by replacing D-glucose with another sugar (e.g., D-xylose, D-galactose, or maltose) in the method for measuring the glucose dehydrogenase activity described in Section 1-1 above, and comparing the results with the results of the D-glucose activity. For comparison, the concentration of each sugar is 50 mM.

The FGDH of the invention having such excellent substrate specificity is preferably used as an enzyme for accurately measuring the amount of glucose in a sample. Specifically, the FGDH of the invention makes it possible to accurately measure the amount of target D-glucose even when the sample contains impurities, such as maltose, D-galactose, and D-xylose. Therefore, the enzyme of the invention is considered to be suitable for applications where impurities in a sample are a concern or expected (typically, suitable for measuring the amount of glucose in blood). In addition to these applications, this enzyme is also applicable to various applications and is highly versatile.

1-4. Affinity for D-Glucose

The FGDH of the invention preferably has high affinity for D-glucose, which is its natural substrate. Due to high affinity, even when a sample contains D-glucose at a low concentration, the catalytic reaction described above can proceed. Further, such high affinity contributes to more accurate measurement of the D-glucose concentration, the measurement in a shorter period of time, and the measurement with the use of smaller amount of enzyme. The affinity of FDGH for D-glucose is expressed as a Km value. A Km value is calculated from a so-called Michaelis-Menten equation. Specifically, a Km value is calculated by varying the D-glucose concentration in the activity measurement method described in Section 1-1 above, and measuring the activity in each concentration to create a Lineweaver-Burk plot.

According to enzyme kinetics, an enzyme having a lower Km value has a higher affinity for a substrate, and the enzyme can form a complex with the substrate even at a low substrate concentration, allowing the catalytic reaction to proceed at a faster rate. The FGDH of the invention has a Km value for D-glucose of preferably 16 mM or less, more preferably 14 mM or less, still more preferably 12 mM or less, even more preferably 10 mM or less, and further preferably 8.2 mM or less.

1-5. Optimal Activity pH

The FGDH of the invention preferably has the highest activity at a pH of 8.0 (Tris-HCl buffer solution), as shown in the Examples below. Further, at a pH of 7.0 to 8.0 (Tris-HCl buffer solution), pH of 6.5 to 7.5 (potassium phosphate buffer solution), or pH of 6.5 (MES-NaOH buffer solution), the FGDH of the invention preferably has a relative activity of 80% or more, based on the activity at a pH of 8.0 (Tris-HCl buffer solution) taken as 100%. Specifically, the FGDH of the invention has an optimal activity pH of 7.0 to 8.0, and preferably 8.0.

1-6. Optimal Activity Temperature

The FGDH of the invention has an optimal activity temperature of preferably 50 to 55° C. The optimal activity temperature of 50 to 55° C. as used herein typically means that the temperature is more or less within a range of 50 to 55° C., and the range further includes an acceptable allowance to some extent. In this specification, the optimal activity temperature can be calculated by measuring the enzyme activity in PIPES-NaOH buffer (pH 6.5) at an enzyme concentration of 0.1 U/mL, as shown in the Examples below.

1-7. pH Stability

In this specification, when 2 U/mL of enzyme that has been treated at 25° C. for 16 hours under specific pH conditions has remaining enzyme activity of 95% or more, compared to the enzyme activity of the same enzyme before treatment, this enzyme is considered to be stable under these pH conditions. The FGDH of the invention is preferably stable at least within the entire pH range of 3.0 to 8.5.

1-8. Temperature Stability

In this specification, when 2 U/mL of enzyme that has been treated for 15 minutes in an appropriate buffer solution (e.g., potassium acetate buffer (pH of 5.0)) under specific temperature conditions has remaining enzyme activity that is not substantially reduced, compared to the enzyme activity of the same enzyme before treatment (i.e., when about 90% or more, preferably 95% or more, of the enzyme activity remains), this enzyme is considered to be stable under these temperature conditions. The FGDH of the invention is preferably stable at least at a temperature of 55° C. or lower (i.e., within the temperature range of 0 to 55° C.).

The FGDH of the invention preferably has at least one, more preferably 2 or more, still more preferably 3 or more, even more preferably 4 or more, further preferably 5 or more, yet further preferably 6 or more, and particularly preferably all, of the characteristics described in Sections 1-3 to 1-8 above. The FGDH of the invention may have any combination of the characteristics described in Sections 1-3 to 1-8 above. It is preferable that the FGDH of the invention has the characteristics described in Sections 1-3, 1-4, 1-7, and 1-8 above.

1-9. Molecular Weight

The polypeptide moiety constituting the FGDH of the invention preferably has a molecular weight of about 68 kDa as measured by SDS-PAGE. The "about 68 kDa" includes a range in which a person skilled in the art would usually determine that the band is present at a position of 68 kDa when a molecular weight is measured by SDS-PAGE. The "polypeptide moiety" refers to FGDH substantially not having an attached sugar chain. When the FGDH of the invention produced by microorganisms is in a glycosylated form, heat treatment or glycohydrolase treatment may be performed so that the sugar chains are removed (i.e., so that the "polypeptide moiety" is obtained). The state of "substantially not having an attached sugar chain" allows the existence of sugar chains necessarily remaining after heat treatment or glycohydrolase treatment of the FGDH in a glycosylated form. Therefore, when FGDH is originally not in a glycosylated form, the FGDH itself corresponds to the "polypeptide moiety."

The means for removing sugar chains from FGDH in a glycosylated form is not particularly limited. For example, as shown in the Examples below, the sugar chains can be removed by denaturing the FGDH in a glycosylated form by heat treatment at 100° C. for 10 minutes, followed by treatment at 37° C. for 6 hours with N-glycosidase F (produced by Roche Diagnostics K.K.).

When the FGDH of the invention has an attached sugar chain, its molecular weight is not limited, as long as no adverse effect is made on the glucose dehydrogenase activity, substrate specificity, affinity for D-glucose, or the like. For example, when the FGDH of the invention has an attached sugar chain, the molecular weight is preferably 122,000 to 154,000 Da as measured by SDS-PAGE. The FGDH in a glycosylated form is preferable, considering that it better stabilizes the enzyme, and enhances water solubility to be easily dissolved in water.

The molecular weight measurement by SDS-PAGE may be performed using general techniques and devices with the use of commercially available molecular weight markers.

1-10. Origin

The origin of the FGDH of the invention is not particularly limited, as long as the FGDH has the characteristics described above. The FGDH of the invention can be derived from, for example, microorganisms belonging to the genus *Mucor*. The microorganisms belonging to the genus *Mucor* are not particularly limited. Examples include *Mucor* RD056860. *Mucor* RD056860 is maintained in the international cooperation department of the National Institute of Technology and Evaluation (NITE) Biological Resource Center and can be obtained after completing predetermined procedures.

Examples of other organisms from which the FGDH of the invention is derived include microorganisms living in soils, rivers, lakes, and other water systems; microorganisms living in oceans; microorganisms indigenously present in the surface of or inside various animals or plants, and the like. As an isolation source, it is also possible to use microorganisms that thrive in low-temperature environments; high-temperature environments such as volcanoes; anoxic, high-pressure, and aphotic environments such as deep seas; and special environments such as oil fields.

In addition to FGDH directly isolated from microorganisms, the FGDH of the invention also includes FGDH obtained through protein engineering methods by which the amino acid sequence, etc., of isolated FGDH has been modified, or FGDH obtained through genetic engineering techniques by which the isolated FGDH has been modified. For example, it is possible to use enzymes that are isolated from, for example, microorganisms of the family Mucoraceae, more specifically, microorganisms of the genus *Mucor*, the genus *Absidia*, or the genus *Actinomucor*, and that are modified to have the characteristics described above. Even more specifically, modified enzymes obtained by modifying enzymes from microorganisms belonging to *Mucor guilliermondii*, *Mucor prainii*, *Mucor javanicus*, *Mucor circinelloides*, *Mucor hiemalis f. silvaticus*, or *Mucor subtilissimus* may also be used.

2. DNA Encoding Flavin-Binding Glucose Dehydrogenase

The DNA of the invention encodes the FGDH described in Section 1 above. Specifically, the DNA of the invention is any one of the following (A) to (F):

(A) DNA encoding the amino acid sequence of SEQ ID NO: 1;
(B) DNA having the base sequence of SEQ ID NO: 2;
(C) DNA having a base sequence with 80% or more homology to the base sequence of SEQ ID NO: 2, and encoding a polypeptide having glucose dehydrogenase activity;
(D) DNA hybridizing to a base sequence complementary to the base sequence of SEQ ID NO: 2 under stringent conditions, and encoding a polypeptide having glucose dehydrogenase activity;
(E) DNA having the base sequence of SEQ ID NO: 2 in which one or several bases are substituted, deleted, inserted, added, and/or inverted, and encoding a polypeptide having glucose dehydrogenase activity; and
(F) DNA having the amino acid sequence of SEQ ID NO: 1 in which one or several amino acid residues are substituted, deleted, inserted, added, or inverted, and encoding a polypeptide having glucose dehydrogenase activity.

As used herein, the phrase "DNA encoding a protein" refers to DNA from which the protein is obtained when the DNA is expressed. Specifically, the "DNA encoding a protein" refers to DNA having a base sequence corresponding to the amino acid sequence of the protein. Therefore, the "DNA encoding a protein" also includes the DNA that varies according to codon degeneracy.

The DNA of the invention has a base sequence with 80% or more, preferably 85% or more, more preferably 88% or more, still more preferably 90% or more, even more preferably 93% or more, further preferably 95% or more, particularly preferably 98% or more, and most preferably 99% or more, homology to the base sequence of SEQ ID NO: 2, as long as the protein having the amino acid sequence encoded by this DNA has glucose dehydrogenase activity and preferably at least one characteristic from among the characteristics described in Sections 1-2 to 1-10 above (particularly characteristics described in Sections 1-3, 1-4, 1-7, and 1-8).

The base sequence homology can be calculated using a commercially available analytical tool or an analytical tool available through telecommunication lines (Internet). For example, software, such as FASTA, BLAST, PSI-BLAST, or SSEARCH, is used for the calculation. Specifically, the main initial conditions generally used in a BLAST search are as follows: in Advanced BLAST 2.1, a blastn program is used, and the parameters are set to default values to perform a search to thereby obtain a homology value (%) of a nucleotide sequence.

The DNA of the invention may be DNA hybridizing to a base sequence complementary to the base sequence of SEQ ID NO: 2 under stringent conditions, as long as the protein coded by this DNA has glucose dehydrogenation activity and preferably at least one characteristic from among characteristics described in Sections 1-2 to 1-10 above, and more preferably Sections 1-3, 1-4, 1-7, and 1-8. The "stringent conditions" as used herein refer to conditions under which a specific hybrid is formed, while a non-specific hybrid is not formed. Such stringent conditions are known to a person skilled in the art and may be established with reference to, for example, Molecular Cloning (Third Edition, Cold Spring Harbor Laboratory Press, New York) or Current Protocols in Molecular Biology (edited by Frederick M. Ausubel et al., 1987).

Examples of specific stringent conditions include conditions in which a hybridization solution (50% formamide, 10×SSC (0.15 M NaCl, 15 mM sodium citrate, pH of 7.0), 5×Denhardt's solution, 1% SDS, 10% dextran sulfurate, 10 µg/mL of denatured salmon sperm DNA, and 50 mM phosphoric acid buffer (pH of 7.5)) is used, and incubation is carried out at about 42 to 50° C., followed by washing at about 65 to 70° C. with 0.1×SSC and 0.1% SDS. More preferable examples of the stringent conditions include conditions in which 50% formamide, 5×SSC (0.15 M NaCl, 15 mM sodium citrate, pH of 7.0), 1×Denhardt's solution, 1% SDS, 10% dextran sulfate, 10 µg/mL of denatured salmon sperm DNA, and 50 mM phosphoric acid buffer (pH of 7.5) are used as a hybridization solution.

DNA that undergoes hybridization under the above conditions possibly includes DNA containing a stop codon in the middle, or DNA whose activity is abolished as a result of the mutation in the active center. However, such DNA can be easily removed by introducing it into a commercially available active expression vector, expressing it in a suitable host, and determining the enzyme activity using known techniques.

In terms of the DNA described in (E) and (F) above, the term "several" is as defined in Section 1-2 above. Specifically, the term "several" as used herein indicates a number corresponding to, for example, less than about 20%, preferably less than about 15%, still more preferably less than about 10%, even more preferably less than about 5%, and most preferably less than about 1%, of the total DNA, as long as the glucose dehydrogenase activity and preferably the characteristics described in Sections 1-3 to 1-10 (in particular, Sections 1-3, 1-4, 1-7, and 1-8) below are not impaired. More specifically, the number of mutated bases is, for example, 2 to 382, preferably 2 to 286, more preferably 2 to 290, still more preferably 2 to 95, even more preferably 2 to 19, further preferably 2 to 15, yet further preferably 2 to 10, and the most preferably 2 to 5.

In a preferable embodiment, DNA encoding the FGDH of the invention is present in an isolated state. As used herein, DNA in an "isolated" state means that the DNA is separated from components such as other nucleic acids and proteins that coexist in nature. However, it is possible for the isolated DNA to contain a portion of other nucleic acid components, such as nucleic acid sequences (e.g., promoter region sequences and terminator sequences) that naturally flank the DNA sequence. For example, chromosomal DNA in an isolated state is preferably substantially free of other DNA components coexisting in nature. When DNA prepared by genetic engineering techniques, such as cDNA molecules, is in an isolated state, it is preferably substantially free of cell components, culture media, and the like. Likewise, when DNA prepared by chemical synthesis is in an isolated state, it is preferably substantially free of precursors (starting materials) such as dNTP, as well as chemical substances, etc., used in the synthetic process. When referred to simply as "DNA" in this specification, it means that the DNA is in an isolated state, unless otherwise clearly stated that it has a different meaning. The DNA of the invention also includes DNA (cDNA) complementary to the DNAs described in (A) to (F) above.

The DNA of the invention may be produced or obtained by chemical DNA synthesis based on this specification or the sequence information (in particular SEQ ID NO: 2) in the accompanying Sequence Listing. For example, it is possible to easily prepare the DNA of the invention by using standard genetic engineering techniques, molecular biological techniques, biochemical techniques, and the like (see Molecular Cloning 2nd Ed, Cold Spring Harbor Lab. Press (1989); *Zoku-Seikagaku Jikken Kouza, Idenshi Kenkyuho I, II, III*, [Sequel Biochemical Experiment Lecture, Gene Study Methods I, II, III], 1986, Japanese Biochemical Society ed.; etc.). Examples of chemical DNA synthesis include solid-phase synthesis using a phosphoramidite method. An automated synthesis device may be used in this synthesis.

Standard genetic engineering techniques can be performed, specifically, by preparing a cDNA library from suitable source microorganisms that can express the FGDH of the invention according to a known method, and selecting desired clones using an appropriate probe or antibody specific to the DNA sequence of the invention (e.g., the base sequence of SEQ ID NO: 2) from this library (Proc. Natl. Acad. Sci., U.S.A., 78, 6613; (1981) Science 122, 778 (1983), etc.).

The source microorganisms for preparing a cDNA library are not limited, as long as they express the FGDH of the invention, but are preferably microorganisms of the genus *Mucor*, and more specifically, microorganisms stated in Section 1-10 above.

Separation of total RNA from the above microorganisms, separation and purification of mRNA, production and cloning of cDNA, and the like, may all be carried out using known methods. Methods for screening cDNA libraries for the DNA of the invention are also not limited and can be performed using usual methods. For example, a method may be used in which an immunological screening is performed by using antibodies specific to a polypeptide derived from cDNA to select the corresponding cDNA clones. It is also possible to use a plaque hybridization method or a colony hybridization method using probes that selectively bind to the target nucleotide sequence. Combinations of these methods may also be used.

In obtaining DNA, it is preferable to use PCR (Science 130, 1350 (1985)) or modified versions of PCR, such as DNA or RNA amplification methods. If obtaining full-length cDNA from libraries is difficult, it is preferable to use a RACE method (Rapid amplification of cDNA ends; *Jikken Igaku* [Experimental medicine], 12 (6), 35 (1994)), in particular, a 5'-RACE method (M. A. Frohman, et al., Proc. Natl. Acad. Sci., U.S.A., 8, 8998 (1988)), or the like.

The primers used in PCR may also be suitably designed and synthesized based on the base sequence of SEQ ID NO: 2. As described above, amplified DNA or RNA fragments may be isolated and purified according to known methods, such as gel electrophoresis and hybridization.

The use of the DNA of the invention enables easy and stable production of the FGDH of the invention in large amount.

3. Vector

The vector of the invention contains the DNA encoding the FGDH of the invention described in Section 2 above. The "vector" as used herein is not particularly limited in terms of the type and the structure, insofar as it is a nucleic acid molecule (carrier) that can transfer an inserted nucleic acid molecule to a target such as a cell, it can replicate the DNA of the invention in a suitable host cell, and it can express the DNA of the invention. Specifically, the vector of the invention is an expression vector. An appropriate type of vector is selected in consideration of the type of host cell. Specific examples of vectors include plasmid vectors, cosmid vectors, phage vectors, viral vectors (e.g., adenoviral vectors, adeno-associated viral vectors, retroviral vectors, herpesviral vectors), and the like. Vectors suitably used when filamentous fungi are used as hosts may also be used. It is also possible to use vectors suitable for self-cloning.

In the use of *Escherichia coli* as a host, for example, an M13 phage or modifications thereof, a λ phage or modifications thereof, pBR322 or modifications thereof (e.g., pB325, pAT153, pUC8), and the like may be used. In the use of yeasts as hosts, pYepSec1, pMFa, pYES2, and the like, may be used. In the use of insect cells as hosts, for example, pAc and pVL may be used. In the use of mammalian cells as hosts, for example, pCDM8 and pMT2PC may be used. However, the vectors are not limited to these examples.

An expression vector usually contains, for example, a promoter sequence required for expression of inserted nucleic acid, and an enhancer sequence for facilitating the expression. It is also possible to use an expression vector containing a selection marker. In the use of such an expression vector, whether the expression vector is introduced (and the degree of the introduction) can be confirmed using the selection marker. Insertion of the DNA of the invention into a vector, insertion of a selection marker gene (if required), insertion of a promoter (if required), and the like, may be performed using standard recombinant DNA technology (e.g., well-known methods that use restriction enzymes and DNA ligase, with reference to Molecular Cloning, Third Edition, 1.84, Cold Spring Harbor Laboratory Press, and New York).

4. Transformant

The present invention also relates to a transformant obtained by introducing the DNA of the invention into a host cell. The means for introducing the DNA of the invention into a host cell is not particularly limited. For example, the DNA contained in a vector described in Section 3 above is introduced into a host cell. Host cells are not particularly limited as long as they can express the DNA of the invention to produce FGDH. Specifically, it is possible to use prokaryotic cells, such as *Escherichia coli* and *Bacillus subtilis*; and eukaryotic cells, such as yeast, mold, insect cells, and mammal cells. Examples of *Escherichia coli* used as a host include *Escherichia coli* C600, *Escherichia coli* HB101, *Escherichia coli* DH5α, and the like, and examples of the vectors include pBR322, pUC19, pBluescript, and the like. Examples of yeast used as a host include *Saccharomyces cerevisiae*, *Schizosaccharomyces pombe*, *Candida utilis*, *Pichia pastoris*, and the like, and examples of the vectors include pAUR101, pAUR224, pYE32, and the like. Examples of filamentous fungal cells used as a host include *Aspergillus oryzae*, *Aspergillus niger*, *Mucor hiemalis*, and the like. Additionally, as a host, it is also preferable to use microorganisms that belong to the genus *Mucor* from which the FGDH is isolated. Specifically, although in transformants, foreign DNA is generally present in a host cell, a preferable embodiment also includes transformants obtained by a self-cloning in which microorganisms from which the DNA is derived is used as a host.

The transformant of the invention is preferably obtained by transfection or transformation of the expression vector described in Section 3 above. The transformation may be transient or stable transformation. Transfection or transformation may be performed by a calcium phosphate co-sedimentation method, an electroporation method (Potter, H. et al., Proc. Natl. Acad. Sci. U.S.A. 81, 7161-7165 (1984)), a lipofection method (Felgner, P. L. et al., Proc. Natl. Acad. Sci. U.S.A. 84, 7413-7417 (1984)), a microinjection method (Graessmann, M.& Graessmann, A., Proc. Natl. Acad. Sci. U.S.A. 73, 366-370 (1976)), a Hanahan method (Hanahan, D., J. Mol. Biol. 166, 557-580 (1983)), a lithium acetate method (Schiestl, R. H. et al., Curr. Genet. 16, 339-346 (1989)), a protoplast-polyethylene glycol method (Yelton, M. M. et al., Proc. Natl. Acad. Sci. 81, 1470-1474 (1984)), or the like.

The transformant of the invention is capable of producing the FGDH of the invention. Therefore, the use of the transformant of the invention enables efficient production of the FGDH of the invention.

5. Method for Producing Flavin-Binding Glucose Dehydrogenase

The FGDH of the invention is typically produced by culturing microorganisms that are capable of producing the FGDH of the invention. Microorganisms to be cultured are not particularly limited, as long as they are capable of producing the FGDH of the invention. For example, wild-type microorganisms belonging to the genus *Mucor* mentioned in Section 1 above, and the transformants described in Section 4 above are preferably used.

The microorganisms of the genus *Mucor* are maintained, for example, in the international cooperation department of the NITE Biological Resource Center, and can be obtained after completing predetermined procedures.

The culture method and culture conditions are not limited, as long as the FGDH of the invention is produced. Specifically, as long as FGDH is produced, any method and conditions can be used that are suitable for the growth of the microorganisms to be used. Examples of culture conditions, such as culture medium, culture temperature, and culture period, are described below.

There is no limitation on culture media as long as the microorganisms to be used can grow. Examples include those containing carbon sources such as glucose, sucrose, gentiobiose, soluble starch, glycerin, dextrin, molasses, and organic acids, and further containing ammonium sulfate, ammonium carbonate, ammonium phosphate, and ammonium acetate; and those containing nitrogen sources, such as peptone, yeast extract, corn steep liquor, casein hydrolysate, wheat bran, meat extract, and those containing inorganic salts, such as potassium salts, magnesium salts, sodium salts, phosphoric salts, manganese salts, iron salts, and zinc salts. To promote the growth of the microorganisms, it is also possible to add vitamins, amino acids, etc., to media.

When the FGDH of the invention is obtained by culturing the microorganisms of the genus *Mucor*, the culture conditions may be selected in consideration of nutritional and physiological characteristics of the microorganisms. Liquid culture is performed in many cases. Industrially, it is advantageous to perform aeration-agitation culture. In terms of the productivity, however, performing solid culture may be more advantageous.

The medium has a pH of, for example, about 3 to 8, and preferably about 5 to 7, as long as it is suitable for the growth of microorganisms to be cultured. Culture is performed at a culture temperature of usually about 10 to 50° C., preferably about 25 to 35° C., for 1 to 15 days, preferably about 3 to 7 days, under aerobic conditions. As a culture method, for example, shake culture or aerobic submerged culture using a jar fermentor may be used.

It is preferable that the FGDH is recovered from the culture medium or cells after culture under the above conditions. When microorganisms that secrete FGDH out of the cells are used, the enzyme of the invention can be obtained, for example, in the following manner. Specifically, the culture supernatant is filtered, centrifuged, etc., to remove insoluble matter, and separation and purification are performed by suitably combining the following: ultrafiltration membrane concentration, ammonium sulfate precipitation and other salting out, dialysis, various chromatographies, and the like. A flavin-binding glucose dehydrogenase produced by microorganisms that belong to the genus *Mucor* is basically a secretory protein.

In contrast, when the FGDH is recovered from inside the cells, the enzyme of the invention can be obtained, for example, in the following manner. Specifically, the cells are disrupted by pressure treatment, ultrasonic treatment, mechanical technique, or techniques using enzymes such as lysozyme, and a surfactant and a chelating agent such as EDTA are optionally added to solubilize GDH, which is separated and collected as an aqueous solution, followed by separation and purification. It is also possible to perform this series of processes (cell disruption, separation, and purification) after recovering cells in advance from culture medium by filtration, centrifugation, or the like.

Purification may be performed, for example, by suitably combining vacuum concentration, membrane concentration, salting out with ammonium sulfate or sodium sulfate, fractional precipitation with a hydrophilic organic solvent such as methanol, ethanol, or acetone, heat treatment, isoelectric focusing, gel filtration with an adsorbent or a gel filtration agent, adsorption chromatography, ion-exchange chromatography, affinity chromatography, and the like.

When column chromatography is used, for example, gel-filtration column chromatography using Sephadex gel (produced by GE Healthcare Bioscience) and column chromatography using DEAE Sepharose CL-6B (produced by GE Healthcare Bioscience) or Octyl Sepharose CL-6B (produced by GE Healthcare Bioscience) may be used. It is preferable that the purified enzyme preparation be purified to the extent that the enzyme migrates as a single band on electrophoresis (SDS-PAGE).

In harvesting (e.g., extracting or purifying) a protein having glucose dehydrogenase activity from culture medium, any of the following may be used, singly or multiply, as indices: glucose dehydrogenase activity, action on maltose, thermal stability, and the like.

In each purification process, in principle, the FGDH activity is used as an index for fractionation, thereby proceeding to the next step. This does not apply, however, if the appropriate conditions can be set in advance such as by performing a preliminary test.

To obtain the FGDH of the invention as a purified preparation, purification is preferably performed to the extent that the specific activity is, for example, 150 to 250 (U/mg), and preferably 180 to 220 (U/mg). The final form may either be a liquid or a solid (including a powder).

To obtain the enzyme of the invention as a recombinant protein, various modifications can be made. For example, DNA encoding the enzyme of the invention and other appropriate DNA are inserted into the same vector, which is used to produce a recombinant protein. In this manner, the enzyme of the invention made of a recombinant protein in which arbitrary peptides or proteins are linked together can be obtained. It is also possible to add sugar chains and/or lipid, or to make modifications that cause processing at the N-terminus or C-terminus. These modifications enable simplifying the extraction and purification of recombinant proteins, as well as addition of biological functions, and the like.

6. Method for Measuring Glucose

Methods for measuring glucose using glucose dehydrogenase have already been established in this technical field. The amount or concentration of glucose in various samples can be measured using the FGDH of the invention according to known methods. The mode for the measurement is not limited, as long as the amount or concentration of glucose can be measured by using the FGDH of the invention. For example, the measurement may be performed by causing the FGDH of the invention to act on glucose in a sample, and spectrophotometrically measuring the structural change of the electron acceptor (e.g., DCPIP) associated with glucose dehydrogenation. More specifically, the measurement may be performed according to the method described in Section 1-1 above. According to the present invention, the glucose concentration can be measured by adding the FGDH of the invention to a sample, or by adding the FGDH of the invention to a sample, followed by mixing. The sample containing glucose is not limited. Examples of the samples include blood, beverages, foods, and the like. The amount of enzyme added to a sample is not limited, as long as it is possible to measure the amount or concentration of glucose.

The glucose concentration can be measured using a sensor described later, for example, in the following manner. A buffer solution is placed in a thermostated cell, and the temperature is maintained constant. Potassium ferricyanide, phenazine methosulfate, or the like, can be used as a mediator. An electrode on which the FGDH of the invention is immobilized is used as a working electrode, and a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

7. Glucose Assay Kit

The glucose assay kit of the invention contains the FGDH of the invention in an amount sufficient for at least one assay. In addition to the FGDH of the invention, the kit typically contains a buffer solution and a mediator required for the assay, a glucose standard solution for preparing a calibration curve, and instructions for use. The FGDH of the invention may be provided in various forms, such as a freeze-dried reagent or a solution in an appropriate storage solution.

8. Glucose Sensor

The present invention also provides a glucose sensor that uses the FGDH of the invention. The glucose sensor of the invention can be produced by immobilizing the enzyme of the invention on an electrode, such as a carbon electrode, a gold electrode, or a platinum electrode. Examples of methods for immobilization include a method using a crosslinking reagent, a method for encapsulating the FGDH in a polymer matrix, a method for covering the FGDH with a dialysis membrane, and methods using a photo-crosslinkable polymer, a conductive polymer, a redox polymer, or the like. Alternatively, the FGDH of the invention may be immobilized in a polymer or immobilized adsorptively onto an electrode, together with an electron mediator, such as ferrocene or its derivatives. These methods may also be used in combination. Since the FGDH of the present invention has excellent thermal stability, immobilization may be performed at a relatively high temperature (e.g., 50° C. or 55° C.). Typically, the FGDH of the invention is immobilized on a carbon electrode using glutaraldehyde, followed by treatment with an amine-containing reagent. In this manner, the glutaraldehyde can be blocked.

The glucose concentration can be measured using a sensor in the following manner. A buffer solution is placed in a thermostated cell, and the temperature is maintained constant. Potassium ferricyanide, phenazine methosulfate, or the like, can be used as a mediator. An electrode on which the FGDH of the invention is immobilized is used as a working electrode, and a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

The present invention is more specifically described below by presenting Examples.

EXAMPLES

Example 1

Reconstitution of Strain

Some strains that belong to the genus *Mucor* were obtained from the international cooperation department in the National Institute of Technology and Evaluation (an incorporated administrative agency). Ampules of L-dried strain samples were opened, and 100 µL of reconstitution water was supplied to each sample so as to suspend the dried cells in the water. Thereafter, each suspension was added to a reconstitution medium dropwise, and statically cultured at 25° C. for 3 to 7 days, thereby reconstituting the strain. Sterilized water (distilled water treated in an autoclave at 120° C. for 20 minutes) was used as reconstitution water, and DP medium (dextrin 2.0%, polypeptone 1.0%, $KH_2PO_4$ 1.0%, agarose 1.5%) was used as reconstitution medium.

Example 2

Collection of Culture Supernatant

A loopful of each strain of the genus *Mucor* reconstituted in Example 1 was inoculated in a solid medium containing 2 g of wheat germ and 2 mL of water sterilized in an autoclave at 120° C. for 20 minutes, and was statically cultured at 25° C. for about 3 to 7 days. After the culture, 4 mL of 50 mM potassium phosphate buffer solution (pH of 6.0) containing 2 mM EDTA was added, and the cells were sufficiently suspended by vortex mixing. After a small amount of glass beads were added to the suspension, the cells were disrupted using a beads shocker (Yasui Kikai Corporation) at 3,000 rpm for 3 minutes, twice, followed by centrifugation for 5 minutes at 4° C., 2,000×g. The resulting supernatant was used as a crude enzyme solution.

Example 3

Confirmation of Glucose Dehydrogenase Activity

The activity of glucose dehydrogenase in the crude enzyme solution obtained in Example 2 was measured according to the glucose dehydrogenase activity measurement method shown in Section 1-1 above. Table 1 shows the results.

TABLE 1

| Strain | Activity (U/ml) |
| --- | --- |
| Mucor DR056860 | 0.45 |

As shown in Table 1, GDH activity was confirmed in the crude enzyme solutions from *Mucor* RD056860.

Example 4

Purification of GDH from *Mucor* RD056860

50 mL of DP liquid medium was placed in a 500-mL Sakaguchi flask and sterilized in an autoclave, thereby preparing a preculture medium. A loopful of *Mucor* RD056860 reconstituted in advance in DP plate medium was inoculated in the preculture medium and subjected to shaking culture for 3 days at 25° C., 180 rpm, thereby obtaining a seed culture solution.

Next, 6.0 L of a production medium (yeast extract 2.0%, glucose 1%, pH of 6.0) was placed in a 10-L jar fermenter and sterilized in an autoclave, thereby obtaining a main culture medium. 50 mL of the seed culture solution was inoculated in the main culture medium and was cultured for 3 days under the following conditions: culture temperature=25° C., stirring speed=600 rpm, air flow rate=2.0 L/min, and tube internal pressure=0.2 MPa. Thereafter, the culture solution was filtrated with a filter cloth, thereby collecting fungal cells. The resulting cells were suspended in a 50 mM potassium phosphate buffer solution (pH of 6.0).

The suspension was supplied to a French press (Niro Soavi) at a flow rate of 160 mL/min, and the cells were disrupted at 1,000 to 1,300 bar. Subsequently, ammonium sulfate (Sumitomo Chemical Co., Ltd.) was gradually added to the disrupted cell solution to give 0.2 saturation, and was stirred at room temperature for 30 minutes. Extra precipitates were removed using a filtration adjuvant. Then, the solution was concentrated using a UF membrane (Millipore) having a molecular weight cutoff of 10,000, and the concentrated solution was desalinated using Sephadex G-25 gel. Thereafter, ammonium sulfate was gradually added to the desalinated liquid to give 0.5 saturation, and the resulting liquid was subjected to linear gradient elution with 50 mM phosphate buffer solution (pH of 6.0) by being passed through a 400-mL PS Sepharose Fast Flow column (GE Healthcare) equilibrated in advance with 50 mM potassium phosphate buffer solution (pH of 6.0) containing 0.5-saturated ammonium sulfate. Thereafter, the eluted GDH fraction was concentrated using a hollow fiber membrane (Spectrum Laboratories, Inc.) having a molecular weight cutoff of 10,000, and passed through a DEAE Sepharose Fast Flow column (GE Healthcare), thereby obtaining a purified enzyme. The resulting purified enzyme was subjected to SDS-polyacrylamide gel electrophoresis (PhastGel 10-15% PhastSystem: GE Healthcare). Phosphorylase b (97,400 Da), bovine blood serum albumin (66,267 Da), aldolase (42,400 Da), carbonic anhydrase (30,000 Da), and trypsin inhibitor (20,100 Da) were used as protein molecular weight markers.

The results confirmed the presence of a single band, showing that GDH was fully purified. Further, the mobility compared with the molecular weight markers showed that the molecular weight of FGDH was 122,000 to 154,000 Da.

Example 5

Molecular Weight of Peptide Moiety of Isolated FGDH

The FGDH purified in Example 4 was denatured by heating at 100° C. for 10 minutes, and then treated with 5 U of N-Glycosidase F (Roche Diagnostics.jp) at 37° C. for an hour, thereby decomposing the sugar chain added to the protein. Thereafter, the same measurement as in Example 4 was performed using SDS-polyacrylamide gels electrophoresis. The same molecular weight markers as in Example 4 were used. The results revealed that the molecular weight of the polypeptide moiety of the purified FGDH was about 68,000 Da.

Example 6

Substrate Specificity

According to the above method for measuring the activity of FGDH shown in Section 1-1 above, the activity of the GDH purified in Example 4 was measured with respect to D-glucose, maltose, D-galactose, and D-xylose as substrates. Further, the activities with respect to other sugars relative to the activity (100%) with respect to D-glucose were found. The concentration of each sugar was 50 mM. Table 2 shows the results.

TABLE 2

| Sugar | Relative Activities (%) |
|---|---|
| D-Glucose | 100.0 |
| Maltose | 2.5 |
| D-Galactose | 1.2 |
| D-Xylose | 1.5 |

The results of Table 2 revealed that the apparent activities of FGDH with respect to maltose, D-galactose, and D-xylose were all 2.5% or less, relative to its activity with respect to D-glucose (100%). It was thus shown that FGDH of the present invention has excellent substrate specificity.

Example 7

Optimal Activity pH

The optimal pH was found using the FGDH enzyme liquid (0.5 U/mL) purified in Example 4. An enzyme reaction was performed at 37° C. and different pH values using 100 mM acetic acid-potassium buffer solution (pH of 5.0 to 5.5, plotted with black squares in the figure), 100 mM MES-NaOH buffer solution (pH of 5.5 to 6.5, plotted with white squares in the figure), 100 mM phosphoric acid-potassium buffer solution (pH of 6.0 to 8.0, plotted with black triangles in the figure), and 100 mM tris-HCl buffer solution (pH of 7.5 to 9.0, plotted with white triangles in the figure), so as to compare the relative activities. FIG. 1 shows the results.

The results revealed that the optimal activity of the FGDH of the present invention was the highest at a pH of 8.0 when a tris-HCl buffer solution was used, was the highest in a pH range of 6.5 to 7.0 when a phosphoric acid-potassium buffer solution was used, and was the highest at a pH of 7.0 when a MES-NaOH buffer solution was used. These results showed that the optimal activity pH falls within a range of about 6.5 to 8.0.

Example 8

Optimal Activity Temperature

Figure 2:
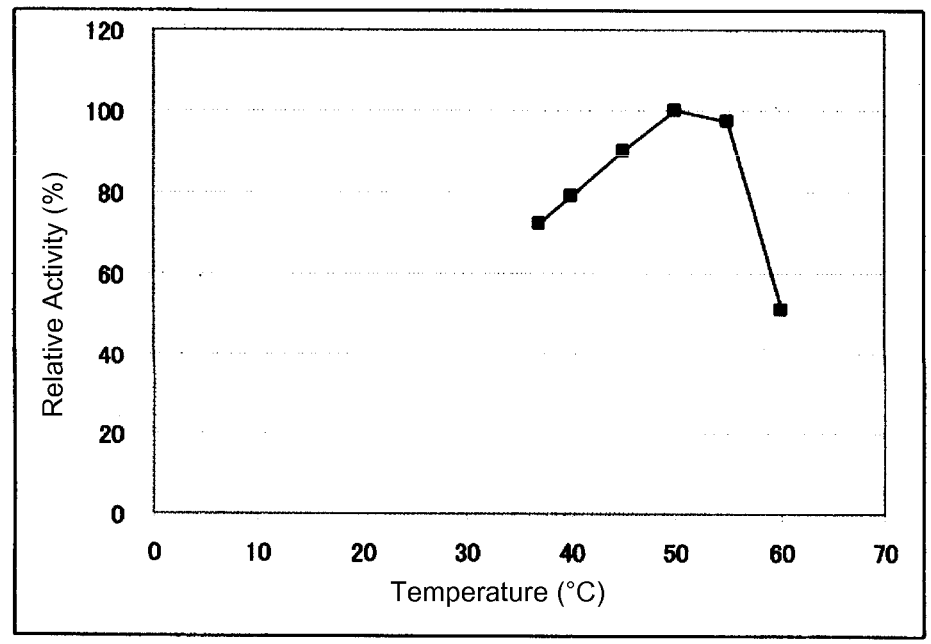
FIG. 2 is a graph showing the influence of temperature on the activity of RD056860-derived FGDH.

The optimal activity temperature was found using the purified FGDH enzyme liquid (0.1 U/mL) obtained in Example 4. The activities at 37° C., 40° C., 45° C., 50° C., 55° C., and 60° C. were measured using a 42 mM PIPES-NaOH buffer solution (pH of 6.5) as a buffer solution. FIG. 2 shows the results.

The results revealed that the activity of the FGDH of the present invention was the highest at a temperature range of 50° C. to 55° C. The activity was 80% or higher with respect to the maximum activity in a range of 40° C. to 55° C. This shows that the optimal activity temperature of the flavin-binding FGDH is in a range of 40° C. to 55° C.

Example 9 pH Stability

Figure 3:
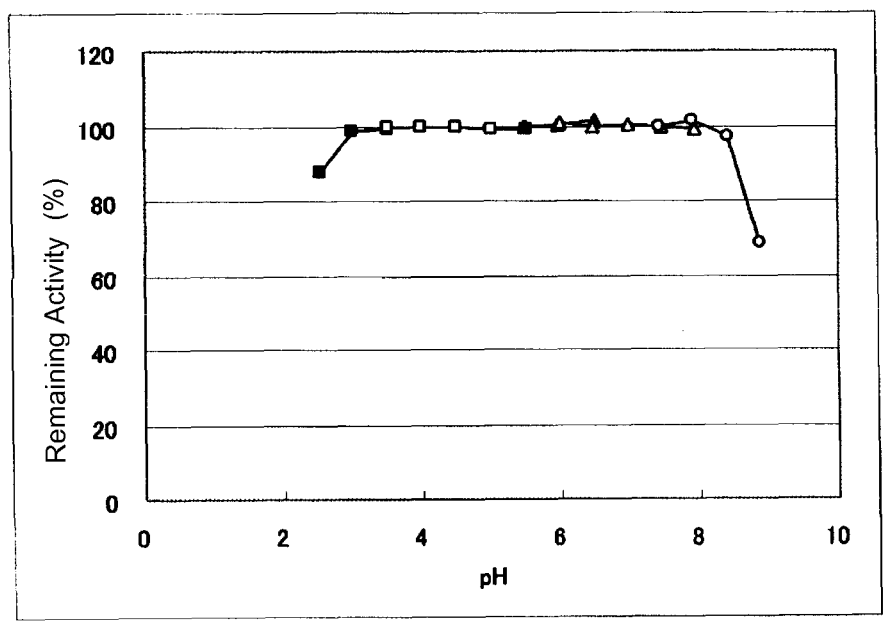
FIG. 3 is a graph showing the measurement results of the pH stability of RD056860-derived FGDH.

The pH stability was measured using the purified FGDH enzyme liquid (2 U/mL) obtained in Example 4. After the enzyme was maintained for 16 hours at 25° C. in 100 mM glycine-HCl buffer solution (pH of 2.5 to 3.5, plotted with black squares in the figure), 100 mM acetic acid-potassium buffer solution (pH of 3.0 to 5.5, plotted with white squares in the figure), 100 mM MES-NaOH buffer solution (pH of 5.5 to 6.5, plotted with black triangles in the figure), 100 mM phosphoric acid-potassium buffer solution (pH of 6.0 to 8.0, plotted with white triangles in the figure), 100 mM tris-HCl buffer solution (pH of 7.5 to 9.0, plotted with black circles in the figure), and 100 mM glycine-NaOH buffer solution (pH of 9.0 to 10.5, plotted with white circles in the figure), the activity was measured using glucose as a substrate. The activity before the treatment and the activity after the treatment were compared to find the remaining activity. FIG. 3 shows the results.

The results revealed that the pH value at which the remaining activity was 95% or more was a pH of 3.0 to 8.5. This shows that the stable pH range is 3.0 to 8.5.

Example 10

Temperature Stability

Figure 4:
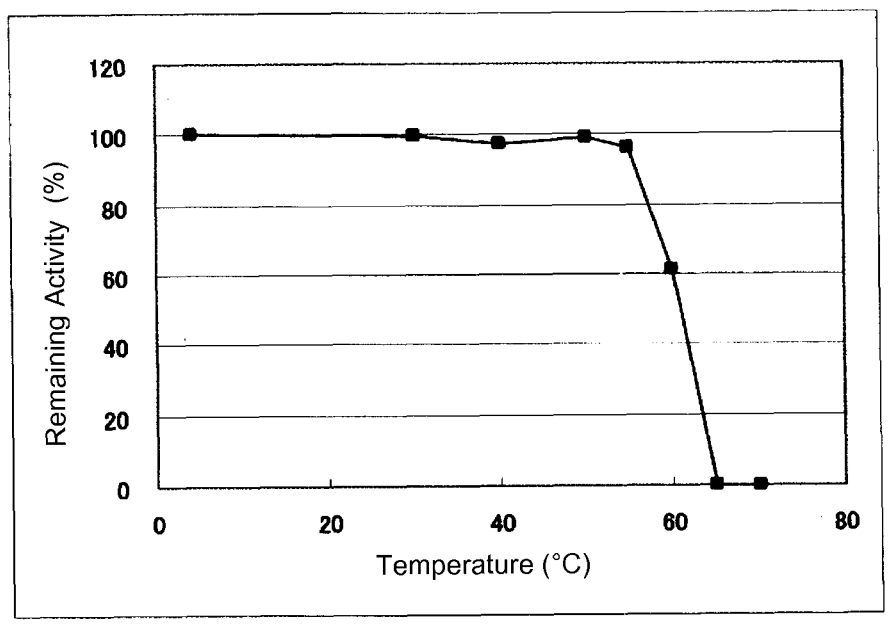
FIG. 4 is a graph showing the measurement results of the temperature stability of RD056860-derived FGDH.

The temperature stability was measured using the purified FGDH enzyme liquid (2 U/mL) obtained in Example 4. The FGDH enzyme liquid was treated with 100 mM potassium acetate buffer solution (pH of 5.0) for 15 minutes at different temperatures (4° C., 30° C., 40° C., 50° C., 55° C., 60° C., 65° C., and 70° C.) thereafter, the GDH activity before the treatment and the GDH activity after the treatment were compared to find the remaining activity. FIG. 4 shows the results.

The results revealed that, after the treatment, the remaining activity of the FGDH of the present invention was 96% at a temperature of 4° C. to 55° C. This showed that the FGDH is stable at a temperature of 55° C. or less.

Example 11

Measurement of Km Value

Figure 5:
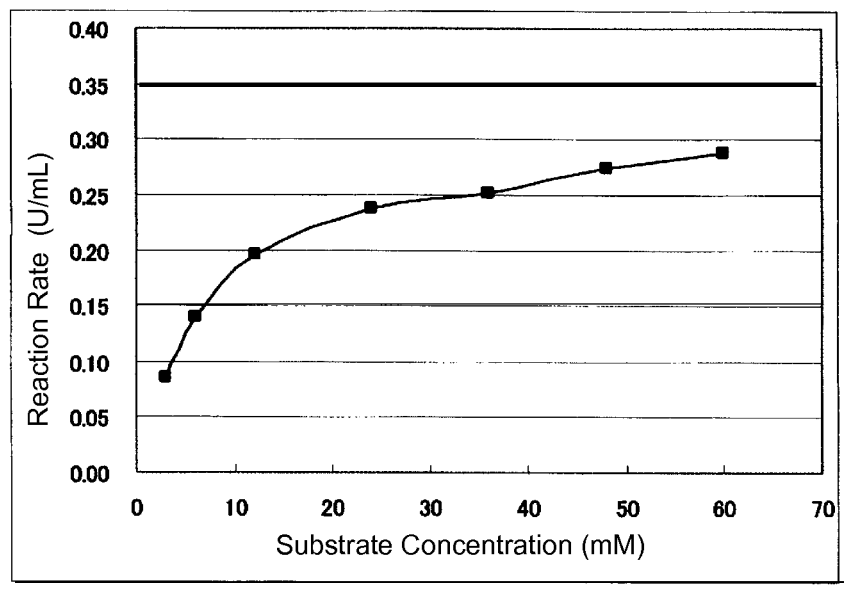
FIG. 5 is a graph showing the relationship between the reaction rate and substrate concentration of RD056860-derived FGDH.

The activity of the FGDH enzyme purified in Example 4 was measured by changing the concentration of D-glucose (substrate), thereby creating a graph of concentration of the substrate against reaction speed (FIG. 5). Based on the graph, a Lineweaver-Burk plot was created to find the Km value of the enzyme with respect to D-glucose. The Km value of the FGDH of the present invention with respect to D-glucose was 8.2 mM.

Example 12

Isolation of DNA Encoding FGDH (1) Extraction of Chromosomal DNA

*Mucor* RD56860 was cultured overnight at 25° C. in a Sakaguchi flask containing 50 ml of YG culture medium (yeast extract 1%, glucose 2%). Thereafter, the culture solution was filtered using a Buchner funnel and a Nutsche suction bottle, thereby obtaining fungal cells. Among the obtained cells, about 0.3 g was frozen in liquid nitrogen, and the hypha was pulverized using a mortar and suspended in 12 ml of an extraction buffer (containing 1% hexadecyltrimethylammonium bromide, 0.7 M NaCl, 50 mM Tris-HCl (pH of 8.0), 10 mM EDTA, and 1% mercapto ethanol). After the suspension was rotationally stirred at room temperature for 30 minutes, the equivalent amount of a solution containing phenol:chloroform:isoamyl alcohol (25:24:1) was added. The mixture was stirred and centrifuged (1,500 g, 5 minutes, room temperature), thereby obtaining a supernatant. The equivalent amount of a solution containing chloroform:isoamyl alcohol (24:1) was added to the resulting supernatant, and the mixture was centrifuged (1,500 g, 5 minutes, room temperature). The equivalent amount of isopropanol was added gently to the resulting supernatant. The resulting precipitate of chromosomal DNA was centrifuged (20,000 g, 10 minutes, 4° C.), and the precipitate resulting from the centrifugation was washed with 70% ethanol and was vacuum-dried. The chromosomal DNA thus obtained was again dissolved in 4 ml of TE, and 200 µL of 10 mg/ml RNase A (Sigma-Aldrich Japan K.K.) was added, followed by incubation at 37° C. for 30 minutes. Then, after 40 µL of 20 mg/ml solution containing Proteinase K, recombinant, PCR Grade (Roche Diagnostics.jp) was added, the mixture was incubated for 30 minutes at 37° C., and the equivalent amount of a solution containing phenol:chloroform:isoamyl alcohol (25:24:1) was added. After stirring, centrifugation (1,500 g, 5 minutes, room temperature) was performed to obtain a supernatant. After the same washing was performed twice, the equivalent amount of a solution containing chloroform:isoamyl alcohol (24:1) was added to the resulting supernatant and stirred, followed by centrifugation (1,500 g, 5 minutes, room temperature). The resulting supernatant was mixed with 3 M NaOAc (pH of 4.8) (1/10 volume of the supernatant) and ethanol (2.5 times the supernatant), and the liquid was centrifuged (20,000 g, 20 minutes, 4° C.), thereby collecting chromosomal DNA. The collected chromosomal DNA was washed with 70% ethanol, vacuum-dried, and finally dissolved in 400 µL TE solution, thereby obtaining a chromosomal DNA solution having a concentration of about 1 mg/ml.

(2) Design of Synthetic Primer

With reference to amino acid sequence of *Aspergillus oryzae*-derived GDH represented by SEQ ID NO: 3 (corresponding to the amino acid sequence of SEQ ID NO: 4 in the sequence listing in U.S. Pat. No. 4,292,486) or other known amino sequences, degenerate primers degeF11 and degeR13 (SEQ ID NOS: 4 and 5) containing mixed bases were synthesized with respect to regions where amino acid sequences are presumably relatively conserved.

(3) Acquisition of Partial Sequence of FGDH Gene by PCR

Using the chromosomal DNA thus obtained in Section (1) above as a template, PCR was performed using DNA polymerase KOD-Plus (Toyobo Co., Ltd.) under recommended conditions. The primers (SEQ ID NOS: 4 and 5) obtained in Section (2) above were used as the primer. The PCR reaction mixture was subjected to agarose gel electrophoresis, and a band of about 1500 bp was confirmed. The amplified DNA fragment was purified and cloned into vector pTA2 using a cloning kit Target Clone-Plus (Toyobo Co., Ltd.) according to the protocol, thereby being introduced into *Escherichia coli* DH5α-strain competent cells (Toyobo Co., Ltd.) to obtain a transformant. The transformant was cultured in LB culture medium, and plasmids were extracted. Then, the base sequence of the region corresponding to the enzyme gene was analyzed. The sequence reaction was performed using a BigDye™ Terminator v3.1 Cycle Sequencing Kit (Applied Biosystems Japan), according to the user's manual of the product. The analysis was performed using an ABI PRISM 310 sequencer (Applied Biosystems Japan). The base sequence analysis of the enzyme gene was performed using a sequence analyzing primer, and the primers mentioned above (SEQ ID NOS: 4 and 5), and Seq 1 (SEQ ID NO: 6). As a result of the base sequence analysis, a partial sequence of FGDH of about 1500 bp was obtained.

(4) Acquisition of Entire Sequence of FGDH Gene

Based on the base sequence thus obtained, two new inverse PCR primers Inv F1 and Inv R1 (SEQ ID NOS: 7 and 8) directed outward from the gene were designed so as to obtain the gene sequence in the N-terminal direction including a start codon. With these inverse PCR primers, inverse PCR was performed using DNA polymerase KOD-Plus (Toyobo Co., Ltd.) under recommended conditions, using, as a template, the chromosomal DNA obtained in Section (1) above treated with restriction enzyme BglII and ligated. The sequence of the amplified fragment was analyzed in the same manner as above, thereby clarifying the upstream base sequence including a sequence assumed to be a start codon. Further, to obtain the gene sequence in the C-terminal direction including a stop codon, inverse PCR was performed in the same manner as above with the above inverse PCR primers Inv F2 and Inv R2 (SEQ ID NOS: 9 and 10), using, as a template, the genomic DNA obtained in Section (1) above treated with restriction enzyme EcoRI and ligated. The sequence of the amplified fragment was analyzed in the same manner as above, thereby clarifying the upstream base sequence including a sequence assumed to be a stop codon.

(5) Determination of N-Terminus and C-Terminus

Using known information to the greatest possible extent, the N-terminus was determined through multilateral comparison with the sequence obtained in Section (4) above in view of homology of amino acid sequences, lengths of base sequences, etc., thereby identifying a start codon. The C-terminus was determined in the same manner.

(6) Design of Primers for Amplifying Entire Length of GDH Gene from *Mucor* RD56860

Based on the determination in Section (5) above, a primer 5UTR F1 (SEQ ID NO: 11) annealing upstream of the start codon, and a primer 3UTR R1 (SEQ ID NO: 12) annealing downstream of the stop codon were designed.

(7) Determination of cDNA Sequence

*Mucor* RD56860 was cultured overnight in a 50-ml YG culture medium (yeast extract 1%, glucose 2%) in a Sakaguchi flask at 25° C. Thereafter, the culture solution was filtered using a Buchner funnel and a Nutsche suction bottle, thereby obtaining fungal cells. Among the obtained cells, about 0.3 g was frozen in liquid nitrogen, and the hypha was pulverized using a mortar. Then, using ISOGEN (Nippon Gene Co., Ltd.), mRNA was obtained from the pulverized cells according to the protocol of the kit. Using this as a template, reverse transcription was performed using ReverTra-Ace (Toyobo Co., Ltd.) according to the protocol, thereby synthesizing cDNA. 3UTR R1 (SEQ ID NO: 12) obtained in Section (6) above was used as a primer for the reverse transcription. Then, using the synthesized cDNA as a template, PCR was performed using DNA polymerase KOD-Plus (Toyobo Co., Ltd.) under recommended conditions. The PCR was performed using the primers (SEQ ID NOS: 11 and 12) obtained in Section (6) above. The PCR reaction mixture was subjected to agarose gel electrophoresis. As a result, a band of about 2000 bp was confirmed. The sequence analysis of the amplified DNA fragment was performed in the same manner as above. In this cDNA sequence analysis, the base sequences of plasmids from three different clones were analyzed. The above primers were used in the base sequence analysis. In this manner, the cDNA sequence of FGDH from *Mucor* RD56860 was determined (SEQ ID NO: 2). The amino acid sequence of the enzyme gene encoded by the cDNA sequence is shown in SEQ ID NO: 1.

(8) Comparison with Known GDH in Terms of Amino Acid Sequence

The identities of the amino acid sequence found in Section (7) above with known FADGDH from *Aspergillus oryzae* and FADGDH from *Aspergillus terreus* were 33% and 33%, respectively. The calculation in the amino acid sequence analysis was performed using a default parameter of the homology algorithm BLAST (Basic Local Alignment Search Tool: http://www.ncbi.nlm.nih.gov/BLAST/) of the National Center for Biotechnology Information (NCBI).

Example 13

Confirmation of Expression and Enzymatic Activity of FGDH from *Mucor* RD056860 in *Aspergillus oryzae*

(1) Construction of Expression Vector

After commercially available *Escherichia coli* competent cells (*E. coli* DH5α: Toyobo Co., Ltd) were transformed with the recombinant plasmid pMspGDH containing *Mucor* RD056860-derived FGDH gene (SEQ ID NO: 2) clarified in Example 12, the transformant was added to a liquid culture medium (1% polypeptone, 0.5% yeast extract, 0.5% NaCl; pH of 7.3) containing ampicillin (50 mg/ml; Nacalai Tesque, Inc.), which was subjected to shaking culture overnight at 30° C. Then a plasmid was prepared from the resulting bacterial cells by using a standard method. The gene region was cleaved by a restriction enzyme and mixed with a vector pUSA cleaved by the same enzyme. The equivalent amount of a ligation reagent (Ligation high: Toyobo Co., Ltd.) was added to the mixed solvent, and the resulting mixture was incubated for ligation. The thus-ligated DNA was introduced into *Escherichia coli* DH5α strain competent cells (Competent High DH5α: Toyobo Co., Ltd.) according to the protocol included, thereby obtaining a transformant. The transformant was cultured in LB medium, thereby extracting a plasmid. In this manner, pUSAMsp GDH capable of mass expression in *Aspergillus oryzae* was obtained.

(2) Transformation

Thereafter, *Aspergillus oryzae* was also transformed with the DNA. The transformation was performed according to the method disclosed in Biosci. Biotech. Biochem., 61(8)1367-1369. 1997. The strain was the same as disclosed in Biosci. Biotech. Biochem., 61(8)1367-1369. 1997, and was obtained from the National Research Institute of Brewing, together with pUSAR plasmid.

(3) Culture

The resulting transformant was cultured using a 10-L jar fermenter (BMS10-PI: Biott Corporation). The transformant was cultured in a medium containing 5% yeast extract, 2% Hinute AM, and 5% Sunmalt (medium liquid amount=7.0 L, stirring speed=600 rpm, temperature=30° C., air flow rate=1.0 vvm). Then, the GDH activity of the crude enzyme solution thus obtained was confirmed. The GDH activity was not observed in the host before the transformation.

This invention is not limited to the above Embodiments and Examples. The invention also includes variations and modifications within the scope of the patent claims set forth below and within a range readily conceived of by those skilled in the art.

The entire content of papers, laid-open patent applications, and patent publications referred to in this specification is incorporated herein by reference.

INDUSTRIAL APPLICABILITY

The FGDH of the invention has excellent substrate specificity, and is capable of more accurately measuring the amount of glucose. The FGDH of the invention is thus suitable, for example, for measuring blood glucose levels.

The invention claimed is:

1. A glucose assay kit, comprising:
a flavin-binding glucose dehydrogenase, the flavin-binding glucose dehydrogenase comprising a polypeptide having an amino acid sequence with 80% or more identity to the amino acid sequence of SEQ ID NO: 1, and having glucose dehydrogenase activity;
and a mediator.

2. A glucose sensor, comprising:
a flavin-binding glucose dehydrogenase immobilized on an electrode, the flavin-binding glucose dehydrogenase comprising a polypeptide having an amino acid sequence with 80% or more identity to the amino acid sequence of SEQ ID NO: 1, and having glucose dehydrogenase activity.

3. The glucose assay kit according to claim 1, further comprising a buffer solution.

4. The glucose sensor according to claim 2, wherein the electrode is selected from one of the following electrodes:
carbon electrode, platinum electrode and gold electrode.

5. The glucose assay kit according to claim 1, wherein the polypeptide having an amino acid sequence with 80% or more identity to the amino acid sequence of SEQ ID NO: 1 is a polypeptide having an amino acid sequence with 85% or more identity to the amino acid sequence of SEQ ID NO: 1.

6. The glucose assay kit according to claim 1, wherein the polypeptide having an amino acid sequence with 80% or more identity to the amino acid sequence of SEQ ID NO: 1 is a polypeptide having an amino acid sequence with 90% or more identity to the amino acid sequence of SEQ ID NO: 1.

7. The glucose assay kit according to claim 1, wherein the polypeptide having an amino acid sequence with 80% or more identity to the amino acid sequence of SEQ ID NO: 1 is a polypeptide having an amino acid sequence with 95% or more identity to the amino acid sequence of SEQ ID NO: 1.

8. The glucose assay kit according to claim 1, wherein the polypeptide having an amino acid sequence with 80% or more identity to the amino acid sequence of SEQ ID NO: 1 is a polypeptide having an amino acid sequence with 98% or more identity to the amino acid sequence of SEQ ID NO: 1.

9. The glucose assay kit according to claim 1, wherein the polypeptide having an amino acid sequence with 80% or more identity to the amino acid sequence of SEQ ID NO: 1 is a polypeptide having an amino acid sequence with 99% or more identity to the amino acid sequence of SEQ ID NO: 1.

10. The glucose sensor according to claim 2, wherein the polypeptide having an amino acid sequence with 80% or more identity to the amino acid sequence of SEQ ID NO: 1 is a polypeptide having an amino acid sequence with 85% or more identity to the amino acid sequence of SEQ ID NO: 1.

11. The glucose sensor according to claim 2, wherein the polypeptide having an amino acid sequence with 80% or more identity to the amino acid sequence of SEQ ID NO: 1 is a polypeptide having an amino acid sequence with 90% or more identity to the amino acid sequence of SEQ ID NO: 1.

12. The glucose sensor according to claim 2, wherein the polypeptide having an amino acid sequence with 80% or more identity to the amino acid sequence of SEQ ID NO: 1 is a polypeptide having an amino acid sequence with 95% or more identity to the amino acid sequence of SEQ ID NO: 1.

13. The glucose sensor according to claim 2, wherein the polypeptide having an amino acid sequence with 80% or more identity to the amino acid sequence of SEQ ID NO: 1 is a polypeptide having an amino acid sequence with 98% or more identity to the amino acid sequence of SEQ ID NO: 1.

14. The glucose sensor according to claim 2, wherein the polypeptide having an amino acid sequence with 80% or more identity to the amino acid sequence of SEQ ID NO: 1 is a polypeptide having an amino acid sequence with 99% or more identity to the amino acid sequence of SEQ ID NO: 1.

* * * * *

SEQUENCE LISTING

```
<160> NUMBER OF SEQ ID NOS: 12

<210> SEQ ID NO 1
<211> LENGTH: 631
<212> TYPE: PRT
<213> ORGANISM: Mucor

<400> SEQUENCE: 1

Met Arg Leu Ser Val Ala Ile Leu Thr Leu Thr Ser Ala Leu Ala Ser
1               5                   10                  15

Val Thr Ser Ala Gln Gln Asn Asn Thr Asp Thr Tyr Asp Tyr Val Ile
            20                  25                  30

Val Gly Gly Gly Val Gly Gly Leu Ala Leu Ala Ser Arg Leu Ser Glu
        35                  40                  45

Asp Lys Asn Val Thr Val Ala Val Leu Glu Ser Gly Pro Tyr Ala Asp
    50                  55                  60

Asp Lys Phe Val Val Tyr Ala Pro Gly Met Tyr Gly Gln Ala Val Gly
65                  70                  75                  80
```

```
Thr Asp Leu Cys Pro Leu Leu Pro Thr Val Pro Gln Pro Ser Met Asn
            85                  90                  95

Asn Arg Thr Ile Thr Ile Ala Thr Gly Arg Leu Leu Gly Gly Gly Ser
            100                 105                 110

Ala Val Asn Gly Leu Val Trp Thr Arg Gly Ala Met Lys Asp Phe Asp
            115                 120                 125

Ala Trp Gln Glu Leu Gly Asn Pro Gly Trp Asn Gly Thr Thr Met Phe
            130                 135                 140

Lys Tyr Phe Lys Lys Ile Glu Asn Phe His Pro Pro Thr Glu Glu Gln
145                 150                 155                 160

Ile Gln Tyr Gly Ala Thr Tyr Asn Lys Ser Val His Gly Phe Asn Gly
                    165                 170                 175

Pro Ile Asp Ile Ala Phe Pro Val Phe Glu Phe Pro Gln Ser Ala Asn
                180                 185                 190

Trp Asn Ala Ser Leu Ala His Leu Asn Phe Thr Arg Arg Gln Asp Leu
            195                 200                 205

Leu Asp Gly Ser Leu His Gly Tyr Ser Thr Thr Pro Asn Thr Leu Asn
210                 215                 220

Pro Gln Thr Ala Arg Arg Ala Asp Ala Tyr Ala Gly Tyr Ile Gln Pro
225                 230                 235                 240

Asn Val Asn Arg Thr Asn Leu Ala Val Leu Ala Asn His Thr Val Ser
            245                 250                 255

Arg Ile Gln Phe Glu Ala Arg Asn Gly Ser Gln Pro Leu Lys Ala Ile
            260                 265                 270

Gly Val Glu Trp Tyr Thr Thr Gly Gly Asp Lys Thr Ser Lys Gln Thr
            275                 280                 285

Ile Lys Ala Arg Arg Glu Ile Ile Leu Ser Ser Gly Ala Ile Gly Ser
290                 295                 300

Pro Lys Leu Leu Glu Val Ser Gly Ile Gly Asn Lys Ala Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Asp
                340                 345                 350

Gly Tyr Thr Thr Asn Ser Val Phe Thr Asn Glu Thr Leu Ala Gln Glu
            355                 360                 365

Gln Lys Asp Leu Tyr Tyr Asn Asn Lys Thr Gly Ile Trp Thr Thr Thr
            370                 375                 380

Pro Asn Asn Leu Gly Tyr Pro Ser Pro Ser Gln Leu Phe Thr Asn Thr
385                 390                 395                 400

Thr Phe Lys Ser Gly Lys Glu Phe Ala Ala Met Ile Arg Asn Ser Thr
            405                 410                 415

Asp Lys Tyr Ala Gln Tyr Ala Ala Asn Asn Ala Thr Asn Val Glu
            420                 425                 430

Leu Leu Lys Lys Gln Tyr Ser Ile Val Ala Arg Arg Tyr Glu Glu Asn
            435                 440                 445

Tyr Ile Ser Pro Ile Glu Ile Asn Phe Thr Pro Gly Tyr Gly Gly Thr
            450                 455                 460

Gly Met Ala Asp Leu Gln Asn Lys Lys Tyr Gln Thr Val Asn His Val
465                 470                 475                 480

Leu Val Ala Pro Leu Ser Arg Gly Tyr Thr His Ile Asn Ser Ser Asp
                485                 490                 495
```

Ile Glu Asp Pro Val Val Ile Asp Pro Gln Tyr Tyr Ser His Pro Leu
              500                 505                 510

Asp Val Asp Val His Val Ala Ser Thr Gln Leu Ala Arg Ser Ile Leu
        515                 520                 525

Asn Ala Pro Gly Leu Ala Ser Ile Asn Ser Gly Glu Val Glu Pro Gly
    530                 535                 540

Glu Lys Val Gln Ser Asp Glu Asp Val Arg Lys Trp Leu Ser Asp Asn
545                 550                 555                 560

Val Arg Ser Asp Trp His Pro Val Gly Thr Cys Ala Met Leu Pro Arg
                565                 570                 575

Lys Leu Gly Gly Val Val Asp Ser Lys Leu Lys Val Tyr Gly Thr Ala
            580                 585                 590

Asn Leu Arg Ile Val Asp Ala Ser Ile Ile Pro Leu Glu Ile Ser Ser
        595                 600                 605

His Leu Met Gln Pro Val Tyr Ala Val Ser Glu Arg Ala Ala Asp Ile
    610                 615                 620

Ile Lys Ser Ser Ser Lys Lys
625                 630

<210> SEQ ID NO 2
<211> LENGTH: 1896
<212> TYPE: DNA
<213> ORGANISM: Mucor

<400> SEQUENCE: 2
atgagacttt ctgttgcaat tttaactttg acctctgccc ttgcctctgt gacaagtgcc      60
cagcaaaata atacagatac ttacgattat gttattgttg gtggtggtgt aggagggttg     120
gctttggcta gtagactttc cgaagataaa aatgttactg ttgcagtttt agaatctgga     180
ccttatgccg atgataaatt tgtcgtatat gctccaggaa tgtatggcca agctgttggc     240
actgatctct gtcctcttct tcctactgtg cctcaaccca gtatgaacaa cagaaccatc     300
actattgcta ctggcagatt acttggtggt ggtagtgctg taaatggttt agtctggact     360
cgtggtgcta tgaaagattt tgacgcttgg caagaacttg gtaatcctgg atggaacggt     420
actaccatgt tcaagtactt taaaaagatt gaaaatttcc atcctccac tgaagagcaa      480 atccaatatg gtgccaccta taacaagagt gtccatggtt ttaatggtcc cattgatatt     540
gctttccccg tctttgagtt ccctcaatct gccaactgga acgcttctct tgctcatctc     600
aattttactc gtcgtcaaga tcttttagat ggttctcttc atggttattc tactactccc     660
aatactttga atcctcagac tgcacgtcgt gctgatgctt acgctgggta tattcaacct     720
aacgtaaatc gtacaaacct tgctgtgctc gctaaccaca ctgtgtctcg tattcaattt     780
gaagccagaa acggcagtca acctctcaag gccatcggtg ttgaatggta tactacaggt     840
ggtgataaaa ccagcaagca acaatcaag gcccgtcgtg agatcatcct ttcctctggt      900
gctattggca gccctaagct tttagaagtc tctggtattg gtaacaaggc tatcgttact     960
gccgctggtg ttcaatctct catcgatttg cctggtgttg ttctaacat gcaagatcat     1020 gtccatgccg tcactgtctc tactaccaac atcgatgggt acactaccaa cagtgtattc    1080
accaatgaaa ccttagctca agagcaaaag gacttgtact acaataacaa gacgggtatt    1140
tggaccacca ctcctaacaa cctcggttat cctagtccaa gccagttgtt cacaaacacc    1200
acgttcaagt ctggcaagga attcgctgct atgattcgta acagtacgga caagtatgct    1260
cagtattatg ctgccaataa cgccacgaat gtcgaattgc taagaaaca atattccatt    1320

```
gttgctcgtc gctatgaaga gaattacatt tctcctattg aaataaactt tactcctggt    1380
tatggcggaa ctggtatggc cgatttacaa aacaagaagt atcaaactgt caatcatgtc    1440
cttgttgctc ccttatctcg tggttacacc catatcaatt cttctgatat cgaggaccca    1500
gtggttatcg atcctcaata ctacagtcat cctttggatg tggatgttca tgttgcttct    1560
actcaacttg ctcgctccat cttgaacgct cccggccttg cttctattaa ttctggtgaa    1620
gttgaacctg gagagaaggt gcaatcggat gaggatgttc gcaaatggtt atccgataac    1680
gttcgttctg attggcatcc tgtgggaact tgtgctatgc tgcccagaaa attgggcggt    1740
gtcgttgact ctaaacttaa agtatatgga actgctaatt tacgtattgt tgatgcatca    1800
attatccctc ttgaaatttc ttctcatttg atgcaacctg tgtatgcagt gtccgaaaga    1860
gcagctgata tcatcaagag cagctccaaa aagtag                              1896

<210> SEQ ID NO 3
<211> LENGTH: 593
<212> TYPE: PRT
<213> ORGANISM: Aspergillus oryzae

<400> SEQUENCE: 3

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Glu Ala Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
    130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
    210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270
```

```
Asp Gly Val Glu Ile Thr Ser Ala Asp Gly Lys Val Thr Arg Val His
            275                 280                 285
Ala Lys Lys Glu Val Ile Ile Ser Ala Gly Ala Leu Arg Ser Pro Leu
290                 295                 300
Ile Leu Glu Leu Ser Gly Val Gly Asn Pro Thr Ile Leu Lys Lys Asn
305                 310                 315                 320
Asn Ile Thr Pro Arg Val Asp Leu Pro Thr Val Gly Glu Asn Leu Gln
                325                 330                 335
Asp Gln Phe Asn Asn Gly Met Ala Gly Glu Gly Tyr Gly Val Leu Ala
            340                 345                 350
Gly Ala Ser Thr Val Thr Tyr Pro Ser Ile Ser Asp Val Phe Gly Asn
        355                 360                 365
Glu Thr Asp Ser Ile Val Ala Ser Leu Arg Ser Gln Leu Ser Asp Tyr
370                 375                 380
Ala Ala Ala Thr Val Lys Val Ser Asn Gly His Met Lys Gln Glu Asp
385                 390                 395                 400
Leu Glu Arg Leu Tyr Gln Leu Gln Phe Asp Leu Ile Val Lys Asp Lys
                405                 410                 415
Val Pro Ile Ala Glu Ile Leu Phe His Pro Gly Gly Gly Asn Ala Val
            420                 425                 430
Ser Ser Glu Phe Trp Gly Leu Leu Pro Phe Ala Arg Gly Asn Ile His
        435                 440                 445
Ile Ser Ser Asn Asp Pro Thr Ala Pro Ala Ala Ile Asn Pro Asn Tyr
450                 455                 460
Phe Met Phe Glu Trp Asp Gly Lys Ser Gln Ala Gly Ile Ala Lys Tyr
465                 470                 475                 480
Ile Arg Lys Ile Leu Arg Ser Ala Pro Leu Asn Lys Leu Ile Ala Lys
                485                 490                 495
Glu Thr Lys Pro Gly Leu Ser Glu Ile Pro Ala Thr Ala Ala Asp Glu
            500                 505                 510
Lys Trp Val Glu Trp Leu Lys Ala Asn Tyr Arg Ser Asn Phe His Pro
        515                 520                 525
Val Gly Thr Ala Ala Met Met Pro Arg Ser Ile Gly Gly Val Val Asp
530                 535                 540
Asn Arg Leu Arg Val Tyr Gly Thr Ser Asn Val Arg Val Val Asp Ala
545                 550                 555                 560
Ser Val Leu Pro Phe Gln Val Cys Gly His Leu Val Ser Thr Leu Tyr
                565                 570                 575
Ala Val Ala Glu Arg Ala Ser Asp Leu Ile Lys Glu Asp Ala Lys Ser
            580                 585                 590
Ala
```

<210> SEQ ID NO 4
<211> LENGTH: 23
<212> TYPE: DNA
<213> ORGANISM: Artificial Sequence
<220> FEATURE:
<223> OTHER INFORMATION: The Sequence of designed polinucleotide described in Example

<400> SEQUENCE: 4
ccycargara ayatggghaa ymg       23

<210> SEQ ID NO 5
<211> LENGTH: 26
<212> TYPE: DNA

<213> ORGANISM: Artificial Sequence
<220> FEATURE:
<223> OTHER INFORMATION: The Sequence of designed polinucleotide
      described in Example

<400> SEQUENCE: 5
gcrcadgtdc cvacrggrtg ccartc                                          26

<210> SEQ ID NO 6
<211> LENGTH: 32
<212> TYPE: DNA
<213> ORGANISM: Artificial Sequence
<220> FEATURE:
<223> OTHER INFORMATION: The Sequence of designed polinucleotide
      described in Example

<400> SEQUENCE: 6
gtcccattga tattgctttc cccgtctttg ag                                   32

<210> SEQ ID NO 7
<211> LENGTH: 32
<212> TYPE: DNA
<213> ORGANISM: Artificial Sequence
<220> FEATURE:
<223> OTHER INFORMATION: The Sequence of designed polinucleotide
      described in Example

<400> SEQUENCE: 7
gtcccattga tattgctttc cccgtctttg ag                                   32

<210> SEQ ID NO 8
<211> LENGTH: 30
<212> TYPE: DNA
<213> ORGANISM: Artificial Sequence
<220> FEATURE:
<223> OTHER INFORMATION: The Sequence of designed polinucleotide
      described in Example

<400> SEQUENCE: 8
accatggaca ctcttgttat aggtggcacc                                      30

<210> SEQ ID NO 9
<211> LENGTH: 30
<212> TYPE: DNA
<213> ORGANISM: Artificial Sequence
<220> FEATURE:
<223> OTHER INFORMATION: The Sequence of designed polinucleotide
      described in Example

<400> SEQUENCE: 9
attctggtga agttgaacct ggagagaagg                                      30

<210> SEQ ID NO 10
<211> LENGTH: 34
<212> TYPE: DNA
<213> ORGANISM: Artificial Sequence
<220> FEATURE:
<223> OTHER INFORMATION: The Sequence of designed polinucleotide
      described in Example

<400> SEQUENCE: 10
cacatccaaa ggatgactgt agtattgagg atcg                                 34

<210> SEQ ID NO 11
<211> LENGTH: 34
<212> TYPE: DNA
<213> ORGANISM: Artificial Sequence -continued

```
<220> FEATURE:
<223> OTHER INFORMATION: The Sequence of designed polinucleotide
      described in Example

<400> SEQUENCE: 11
ctccactata taaagctcta tgaattggtg ggag                                34

<210> SEQ ID NO 12
<211> LENGTH: 35
<212> TYPE: DNA
<213> ORGANISM: Artificial Sequence
<220> FEATURE:
<223> OTHER INFORMATION: The Sequence of designed polinucleotide
      described in Example

<400> SEQUENCE: 12
taaaattcac tggccagata aaataaattg aactc                               35
```